(12) United States Patent
Sugaya et al.

(10) Patent No.: US 11,266,539 B2
(45) Date of Patent: Mar. 8, 2022

(54) ADHESIVE TAPE

(71) Applicant: OJI HOLDINGS CORPORATION, Tokyo (JP)

(72) Inventors: Mariko Sugaya, Tokyo (JP); Asami Oda, Tokyo (JP); Ayako Shirai, Tokyo (JP)

(73) Assignee: OJI HOLDINGS CORPORATION, Tokyo (JP)

(*) Notice: Subject to any disclaimer, the term of this patent is extended or adjusted under 35 U.S.C. 154(b) by 665 days.

(21) Appl. No.: 15/781,593

(22) PCT Filed: Jan. 19, 2017

(86) PCT No.: PCT/JP2017/001792
§ 371 (c)(1),
(2) Date: Jun. 5, 2018

(87) PCT Pub. No.: WO2017/130838
PCT Pub. Date: Aug. 3, 2017

(65) Prior Publication Data
US 2020/0261277 A1 Aug. 20, 2020

(30) Foreign Application Priority Data
Jan. 29, 2016 (JP) .............................. JP2016-015954

(51) Int. Cl.
*A61F 13/00* (2006.01)
*A61F 13/02* (2006.01)
(Continued)

(52) U.S. Cl.
CPC ...... *A61F 13/0256* (2013.01); *A61F 13/0259* (2013.01); *A61F 13/06* (2013.01); *A61F 13/10* (2013.01); *A61F 15/001* (2013.01)

(58) Field of Classification Search
CPC .. A61F 13/10; A61F 13/0256; A61F 13/0259; A61F 13/06; A61F 13/064;
(Continued)

(56) References Cited

U.S. PATENT DOCUMENTS 4,930,500 A 6/1990 Morgan
D330,255 S * 10/1992 Nelson, Jr. .................. D24/189
(Continued)

FOREIGN PATENT DOCUMENTS

CN 202313937 U 7/2012
CN 204158557 U 2/2015
(Continued)

OTHER PUBLICATIONS

K. Harada; "Supportive role of nurses in the care for patients treated with EGFR inhibitors;" Journal of Clinical and Experimental Medicine; vol. 241; No. 8; 2012; pp. 588-592 (3 Sheets, 4 Sheets translation. 7 Sheets total)/p. 2 of specification.
(Continued)

*Primary Examiner* — Kim M Lewis
(74) *Attorney, Agent, or Firm* — Kratz, Quintos & Hanson, LLP

(57) ABSTRACT

An adhesive tape (1) comprises a base material layer, an adhesive layer, and a release material layer, wherein two edges (11 and 12) extending in the longitudinal direction of the adhesive tape include parallel portions (11a and 12a), the length of one of the two edges (11 and 12) is greater than the length of the other, the ends of the two edges (11 and 12) are connected to the ends of two other edges (13 and 14), and two angles formed between the longer edge of the two edges (11 and 12) extending in the longitudinal direction and the two other edges (13 and 14) are acute angles.

12 Claims, 6 Drawing Sheets

(51) Int. Cl.
*A61F 13/06* (2006.01)
*A61F 13/10* (2006.01)
*A61F 15/00* (2006.01)

(58) Field of Classification Search
CPC .. A61F 15/001; A61F 13/00072; A61F 13/02; A61F 13/0269; A61F 2013/00089; A61F 2013/00102; A61F 2013/00289; A61F 2013/00361; A61F 2013/00365; A61F 2013/00655; A61F 2013/00897; A61L 15/28; A61L 15/60
USPC .......................................................... D24/189
See application file for complete search history.

(56) References Cited

U.S. PATENT DOCUMENTS

| | | | | |
|---|---|---|---|---|
| 6,384,293 B1 * | 5/2002 | Marcussen | ......... | A61F 13/0259 602/41 |
| D574,085 S * | 7/2008 | Lucchetti | ............ | A61F 13/0259 D24/189 |
| D683,035 S * | 5/2013 | Dunshee | ............. | A61F 13/0259 D24/189 |
| 2003/0138479 A1 * | 7/2003 | Mizota | ................. | A61K 9/7053 424/443 |
| 2006/0042990 A1 * | 3/2006 | Galuten | ............... | B65D 73/005 206/570 |
| 2008/0283426 A1 * | 11/2008 | Primer | .................. | G09F 3/0289 206/232 |
| 2010/0282269 A1 * | 11/2010 | Uchida | ............... | A61F 13/0256 132/200 |
| 2016/0317358 A1 * | 11/2016 | Holm | ................ | A61F 13/0259 |
| 2017/0367896 A1 * | 12/2017 | Holm | ................ | A61F 13/00063 |

FOREIGN PATENT DOCUMENTS

| | | | | |
|---|---|---|---|---|
| DE | 3823889 A1 * | 1/1990 | ........... | A61F 13/068 |
| DE | 3823889 A1 | 1/1990 | | |
| JP | S56-127723 U | 9/1981 | | |
| JP | 2001-517539 A | 10/2001 | | |
| JP | 2002-543921 A | 12/2002 | | |
| JP | 2005-095477 A | 4/2005 | | |
| JP | 2008-264170 A | 11/2008 | | |
| WO | 1999/016396 A1 | 4/1999 | | |
| WO | 2000/069379 A1 | 11/2000 | | |
| WO | 2006120804 A1 | 11/2006 | | |

OTHER PUBLICATIONS

International Search Report for International Application No. PCT/JP2017/001792 dated Apr. 18, 2017 (2 Sheets).

* cited by examiner

Fig. 10

| Self-check sheet 100 | | | | | | | | | | |
|---|---|---|---|---|---|---|---|---|---|---|
| | | | | | | | | | | |
| There is pain around the nail. | No | | | | | | | | | |
| The area surrounding the nail is red and swollen. | Slightly | | | | | | | | | |
| There is cracking of the skin. | No | | | | | | | | | |
| There is itching of the skin. | No | | | | | | | | | |
| . | | | | | | | | | | |
| . | | | | | | | | | | |
| Other points that you have noticed. | | | | | | | | | | |
| | If a symptom is present, consult a doctor or a nurse. | | | | | | | | | |
| Washing | ✓ | | | | | | | | | |
| Moisturizing | ✓ | | | | | | | | | |
| Taping | ✓ | | | | | | | | | |
| Others ( ) | | | | | | | | | | |

ADHESIVE TAPE

CROSS-REFERENCE TO RELATED APPLICATIONS

The present application claims priority to the specification of Japan Patent Application No. 2016-015954 filed on Jan. 29, 2016, the entire contents of which are incorporated herein by reference.

TECHNICAL FIELD

The present invention relates to an adhesive tape.

BACKGROUND ART

There is an increasing number of patients with paronychia (also called "inflammation around nails"), which is a side effect of anticancer agents. Paronychia is inflammation of the skin around fingernails and toenails, and causes often painful redness or swelling on the skin around fingernails and toenails. Conventionally, a commercially available taping material has been used by wrapping it around a nail to relieve pressure on tissue around the nail and the like, prevent increase in severity of inflammation, and relieve pain (Non-patent Literature 1). However, this is cumbersome because a doctor, nurse, patient, or like user must select a taping material from among various commercially available products and cut it to an appropriate size each time for use. Thus, outpatients in particular cannot continue to apply the adhesive tape material, for example, at home, which increases the severity of paronychia.

CITATION LIST

Non-Patent Literature

NPL 1: Journal of Clinical and Experimental Medicine, vol. 241 No. 8 pp. 588-592 (2012)

SUMMARY OF INVENTION

Technical Problem

An object of the present invention is to provide an adhesive tape that enables the prevention and/or treatment of inflammation around nails to be performed conveniently and effectively.

Solution to Problem

To achieve the above object, the present inventors found that an adhesive tape having a specific shape is useful for the prevention and/or treatment of inflammation around nails, and they accomplished the present invention.

Specifically, the present invention is as follows.

Item 1. An adhesive tape comprising a base material layer, an adhesive layer, and a release material layer,
wherein two edges extending in the longitudinal direction of the adhesive tape include parallel portions,
the length of one of the two edges is greater than the length of the other,
the ends of the two edges are connected to the ends of two other edges, and
two angles formed between the longer edge of the two edges extending in the longitudinal direction and the two other edges are acute angles.

Item 2. The adhesive tape according to Item 1, wherein the longer edge of the two edges extending in the longitudinal direction includes a recess toward the inside of the adhesive tape.

Item 3. The adhesive tape according to Item 1 or 2, which has a shape that is symmetrical about a central axis perpendicular to the longitudinal direction of the adhesive tape.

Item 4. The adhesive tape according to Item 3, wherein the release material layer is composed of three portions separated by two slits that are parallel to and equidistant from the central axis, or is composed of two portions separated by one slit on the central axis.

Item 5. The adhesive tape according to any one of Items 1 to 4, which is an adhesive tape for the prevention and/or treatment of inflammation around a nail.

Item 6. A kit for treating paronychia, comprising the adhesive tape according to any one of Items 1 to 5 and a check sheet for recording a state of an affected area.

Item 7. The kit according to Item 6, which further comprises a humectant, a cotton swab, and a protective material.

Item 8. The adhesive tape according to any one of Items 1 to 7, wherein each of the two other edges is substantially straight over its entire length or substantially straight except for both its ends.

Item 9. The adhesive tape according to any one of Items 1 to 8, wherein the two other edges each have a length of 0.8 to 3 cm.

Item 10. The adhesive tape according to any one of Items 1 to 9, wherein the shorter edge of the two edges extending in the longitudinal direction is substantially straight over its entire length or substantially straight except for both its ends.

Advantageous Effects of Invention

The present invention enables the prevention and/or treatment of an affected area, in particular, inflammation of an affected area around nails to be performed conveniently and effectively.

BRIEF DESCRIPTION OF DRAWINGS

FIG. 10 shows an example of a check sheet.

DESCRIPTION OF EMBODIMENTS

Figure 1:
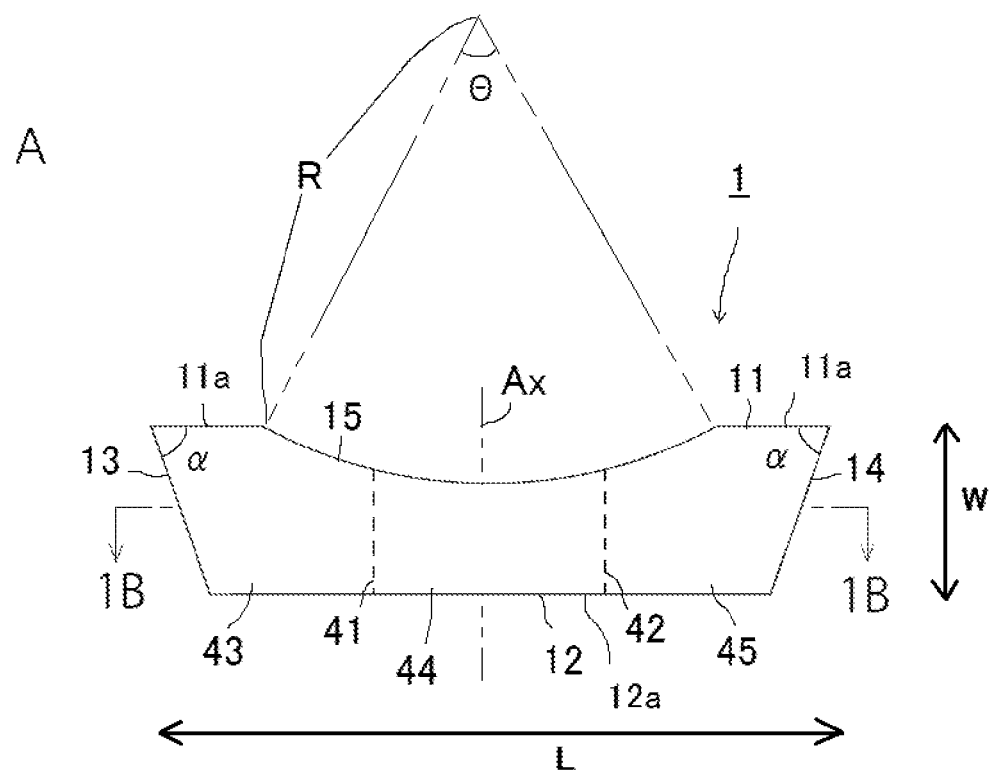
FIG. 1(A) is a plan view of an adhesive tape according to a first embodiment of the present invention.
FIG. 1(B) is a cross-sectional view of the adhesive tape taken along the 1B-1B line of FIG. 1(A).
Figure 1:
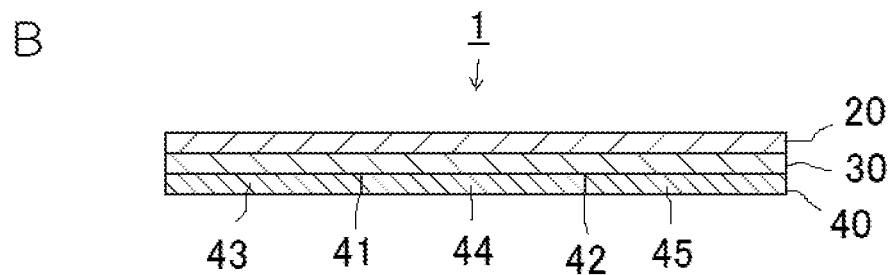

"Prevention and/or treatment" used herein means prevention, treatment, or both prevention and treatment.

An adhesive tape according to a first embodiment of the present invention is described below with reference to FIGS. 1(A), 1(B), 2(A), and 2(B).

FIG. 1(A) is a plan view of an adhesive tape 1 according to the first embodiment of the present invention. FIG. 1(B) is a cross-sectional view of the adhesive tape taken along the 1B-1B line of FIG. 1(A).

As shown in FIG. 1(B), the adhesive tape 1 according to the first embodiment comprises a base material layer 20, an adhesive layer 30, and a release material layer 40. Specifically, the adhesive tape 1 according to the first embodiment is an adhesive tape configured in such a manner that the release material layer 40 is releasably stacked on one surface of the base material 20 with the adhesive layer 30 interposed between them.

As shown in FIG. 1(A), the adhesive tape 1 according to the first embodiment includes a first group of an upper edge 11 and a lower edge 12 extending in the longitudinal direction of the adhesive tape 1, and a second group of a left edge 13 and a right edge 14. The upper edge 11 and the lower edge 12 respectively include substantially straight portions 11a and 12a that are parallel to each other, and the ends of the upper edge 11 and the lower edge 12 are connected to the ends of the substantially straight left edge 13 and right edge 14.

The length of the upper edge 11 is greater than that of the lower edge 12, and the upper edge 11 is connected to the left edge 13 and the right edge 14 at an angle α. The left edge 13 and the right edge 14 are connected to the lower edge 12 at the ends that are opposite to the ends connected to the upper edge 11.

The adhesive tape 1 has a shape that is symmetrical about the central axis Ax perpendicular to the longitudinal direction. That is, the adhesive tape 1 has a shape that is symmetrical about the plane of the adhesive tape 1 that is centered in the longitudinal direction. The angle α is acute and generally 30° or more but less than 90°. The upper edge 11 is provided with a recess 15 curved toward the inside of the adhesive tape. In this embodiment, the recess 15 is formed so as to be arc-shaped in plan view, and it is preferred that R=35 to 137 mm and 0=25 to 90°. The recess 15 functions to enhance the fit of the adhesive tape 1 to a patient's finger, as described later.

The length L of the adhesive tape 1 is not particularly limited and is preferably 4 to 8 cm. The width W of the adhesive tape 1 is not particularly limited and is preferably 0.5 to 2.5 cm. The ratio of the length L to the width W is not particularly limited and is preferably 10:1 to 2:1. The length of the upper edge 11 is preferably 2 to 8 cm, the length of the lower edge 12 is preferably 1.5 to 7.5 cm, and the length of the left edge 13 and length of the right edge 14 are each preferably 0.8 to 3 cm.

The base material layer 20 preferably has elasticity in order to allow for less discomfort upon application to the skin. When the base material layer 20 has elasticity, the adhesive tape 1 easily conforms to the skin and is resistant to becoming detached. The base material layer 20 also preferably has excellent moisture permeability in order to prevent stuffiness at and around an affected area of paronychia due to the adhesive tape 1.

Examples of materials of the base material layer 20 include base materials having elasticity, such as films, nonwoven fabrics, cotton fabrics, knitted fabrics, and laminated composites of a nonwoven fabric and a film. Examples of materials of these base materials include polyethylene, polypropylene, polyethylene terephthalate, polybutylene terephthalate, polyethylene naphthalate, polystyrene, polyamides, polyolefins, nylon, cotton, pulp, acetate rayon, rayon, rayon/polyethylene terephthalate composites, polyacrylonitrile, polyvinyl alcohol, acrylic polyurethane, ester polyurethane, ether polyurethane, styrene-isoprene-styrene copolymers, styrene-butadiene-styrene copolymers, styrene-ethylene-propylene-styrene copolymers, ethylene-vinyl acetate copolymers, and the like.

The base material layer 20 may also comprise components widely used in the art, such as strength control agents, inorganic powders and like extenders, dyes, and pigments. The base material layer 20 may be produced by uniaxial stretching, biaxial stretching, or non-stretching. The base material layer 20 may have a single-layer structure or a multilayer structure in which different kinds or the same kind of layers are stacked.

The thickness of the base material layer 20 is not particularly limited. From the viewpoint of ease of obtaining elasticity and moisture permeability, the thickness of the base material layer 20 is preferably 1000 μm or less, more preferably 500 μm or less, and even more preferably 300 μm or less. On the other hand, from the viewpoint of ease of obtaining strength, the thickness of the base material layer 20 is preferably 15 μm or more, more preferably 20 μm or more, and even more preferably 30 μm or more.

The adhesive layer 30 of the adhesive tape 1 according to this embodiment comprises an adhesive for applying the base material layer 20 to an affected area, which is an object to which the base material layer 20 is to be applied (i.e., adherend).

Examples of adhesives include rubber-based adhesives, acrylic adhesives, silicone-based adhesives, hydrocolloids, and the like. An isocyanate-based crosslinking agent, a metal chelate-based crosslinking agent, a tackifies, etc. may be suitably added to the adhesive in view of adhesion between the adhesive and the base material layer 20 and between the adhesive and the adherend, and adhesive strength. It is preferred that penetration of the adhesive into the skin is suppressed by setting the molecular weight of the adhesive component high.

The thickness of the adhesive layer 30 formed using an adhesive is not particularly limited. In order to obtain moisture permeability, the thickness of the adhesive layer 30 is preferably 100 μm or less, and more preferably 70 μm or less. In order to obtain necessary adhesive strength, the thickness of the adhesive layer 30 is preferably 10 μm or more, and more preferably 20 μm or more. The adhesive layer 30 may also be formed by applying a foam glue. Application may be performed in such a manner that the adhesive layer 30 is formed, for example, in a regular or random pattern, such as a dotted pattern or a stripe pattern.

For the release material layer 40, a known release material used in adhesive tapes may be used. Examples of release materials include paper, plastic films, and the like. The release material layer 40 may be also referred to as release paper.

In order to facilitate peeling off the release material layer 40 at the time of use, the release material layer 40 may have one or more slits. In this embodiment, the release material layer 40 is composed of three portions 43, 44, and 45 separated by two slits 41 and 42 that are parallel to the central axis Ax of the adhesive tape 1 and that are equidistant from the central axis Ax. Thus, the three portions 43, 44, and 45 can be separately peeled off from the positions of the slits 41 and 42 so as to expose the adhesive layer 30 according to the time when the release material layer 40 is applied to the skin. Since the release material layer 40 has the slits 41 and 42, a decrease in adhesive strength due to contact with the adhesive layer 30 upon application can be prevented.

Figure 2:
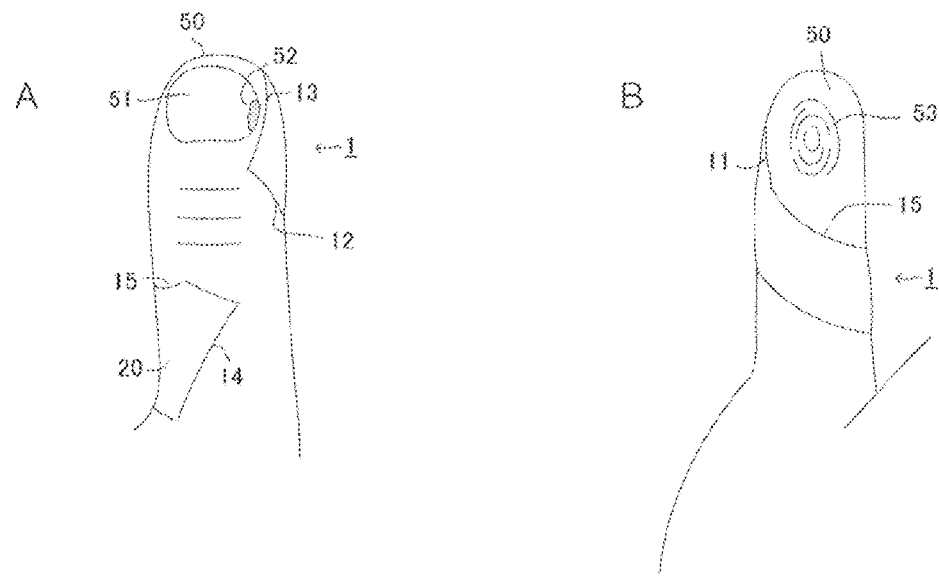
FIG. 2(A) is a schematic view illustrating the adhesive tape of FIG. 1A in use.
FIG. 2(B) is a schematic view illustrating the adhesive tape of FIG. 2(A) when viewed from the pad side of the finger.

Next, the method of use of the adhesive tape 1 is described. As shown in FIG. 2(A), when there is an affected area 52 of paronychia at a site of the skin adjacent to a nail 51 of a thumb 50 of the left hand of a patient, the portion 43 of the release material layer 40 of the adhesive tape 1 is peeled off to expose the corresponding portion of the adhesive layer 30 (in FIG. 1(A), the release material layer 40 is on the underside in plan view). The portion 43 of the release material layer 40 can be easily peeled off by peeling the portion 43 from the position of the slit 41. Subsequently, the left edge 13 of the adhesive tape 1 in which the portion of the adhesive layer 30 corresponding to the portion 43 of the release material layer 40 is exposed is placed on a site of the skin on the side of the affected area 52. The portion 44 of the release material layer 40 is then peeled off to expose the corresponding portion of the adhesive layer 30, and while the adhesive tape 1 is pulled so as to relieve pressure between the nail 51 and the affected area 52, the adhesive tape 1 is applied to the skin helically (obliquely downward) such that the adhesive layer 30 is in contact with the skin. Finally, the portion 45 of the release material layer 40 is peeled off, followed by application to the skin.

In the figure, the adhesive tape 1 ends at the right edge 14 between the first joint and the second joint on the dorsal side of the thumb 50 (on the proximal phalanx). Since the length of the upper edge 11 is greater than that of the lower edge 12 and since the upper edge 11 is at an angle α with respect to the left edge 13 and to the right edge 14, the adhesive tape 1 can be easily applied obliquely downward, thus preventing pressure of the skin on the side of the nail 51 caused by the adhesive tape, as compared with when the length of the upper edge 11 is the same as or shorter than the length of the lower edge 12. In addition, for example, when a between the upper edge 11 and the left edge 13 is 60° to 80°, the right edge 14 is positioned between the first joint and the second joint on the dorsal side of the thumb 50 (on the proximal phalanx). Thus, the range of motion of the finger is unlikely to be limited, and, further, the site of the skin on the side of the affected area 52 can be pulled with appropriate force.

As shown in FIG. 2(B), when viewed from the pad side of the thumb 50, since the upper edge 11 of the adhesive tape 1 has the recess 15, the exposed area of a pad 53 of the fingertip above the first joint of the thumb 50 is larger than that when the upper edge 11 of the adhesive tape 1 is substantially straight. Therefore, sensation of the pad on the fingertip, which is used for many tasks, is less likely to be lost, and easy use in for example, work, household chores, and manipulation of electronic devices, including smartphones, can be maintained.

Further, the adhesive tape 1 is symmetrical with respect to the central axis Ax; thus, if the affected area 52 is on the left side of the nail 51, the adhesive tape 1 can be applied so as to relieve pressure between the nail 51 and the affected area 52 by placing the right edge 14 of the adhesive tape 1 at a site of the skin on the side of the affected area 52 and applying the adhesive tape 1 to the skin helically (obliquely downward).

Figure 3:
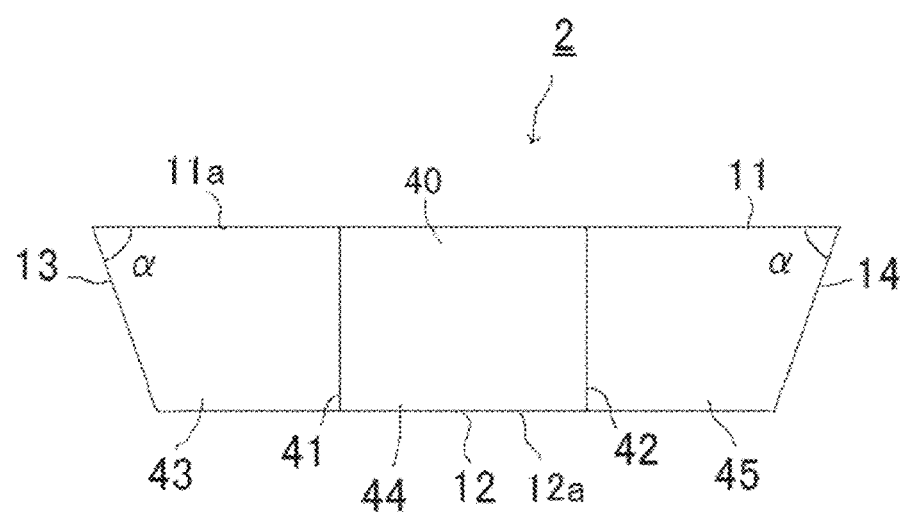
FIG. 3 is a plan view of an adhesive tape according to a second embodiment of the present invention.

With reference to FIG. 3, an adhesive tape according to a second embodiment of the present invention is described below. Elements that are the same as those of the adhesive tape 1 according to the first embodiment are denoted with the same reference numerals as those shown in FIG. 1, and the descriptions are omitted. In FIGS. 3 to 8, which show second to seventh embodiments, adhesive tapes 2 to 7 are shown with the release material layer 40 on the top (on the front in the figure) in plan view.

The adhesive tape 2 according to the second embodiment is different from the adhesive tape 1 according to the first embodiment in that an upper edge 11 does not have a recess 15 and that the entire upper edge 11 is substantially straight. In the adhesive tape 2 according to the second embodiment, the upper edge 11 and lower edge 12 that extend in the longitudinal direction of the adhesive tape 2 and face each other are parallel to each other, the adhesive tape 2 has a shape of an isosceles trapezoid, the upper edge 11 is connected to a substantially straight left edge 13 and right edge 14 at an angle α, and the left edge 13 and the right edge 14 are connected to the lower edge 12 at the ends that are opposite to the ends connected to the upper edge 11. Also with this configuration, the adhesive tape 2 can be applied so as to relieve pressure between the nail 51 and the affected area 52 by placing the left edge 13 or the right edge 14 of the adhesive tape 2 on a site of the skin on the side of the affected area 52 of the patient and applying the adhesive tape 2 to the skin helically (obliquely downward).

Figure 4:
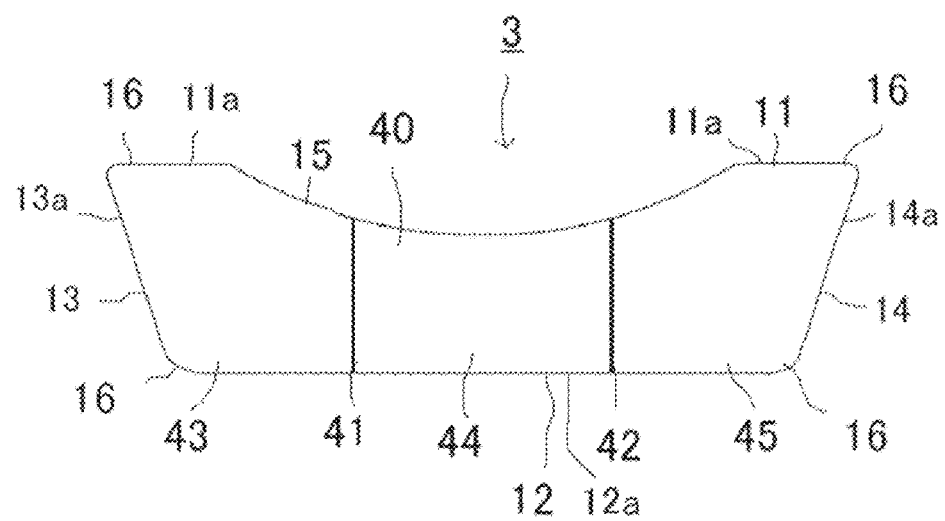
FIG. 4 is a plan view of an adhesive tape according to a third embodiment of the present invention.

With reference to FIG. 4, the adhesive tape according to the third embodiment of the present invention is described below. Elements that are the same as those of the adhesive tape 1 according to the first embodiment are denoted with the same reference numerals as those shown in FIG. 1, and the descriptions are omitted.

The adhesive tape 3 according to the third embodiment is different from the adhesive tape 1 according to the first embodiment in that the four corners 16 of the adhesive tape 3 are rounded. Both ends of an upper edge 11 are rounded in a substantially curved shape, and the upper edge 11 successively includes a substantially straight parallel portion 11a, a recess 15, and a substantially straight parallel portion 11a between both ends. A lower edge 12 is composed of a substantially straight parallel portion 12a except for both its ends that are rounded in a substantially curved shape. A left edge 13 is composed of a substantially straight portion 13a except for both its ends that are rounded in a substantially curved shape, and a right edge 14 is composed of a substantially straight portion 14a except for both its ends that are rounded in a substantially curved shape. The length of each of the substantially straight parallel portions 11a is not particularly limited and is generally 0.5 to 2.5 cm. The length of the substantially straight parallel portion 12a is not particularly limited and is generally 3.0 to 7.3 cm. The lengths of the substantially straight portions 13a and 14a are not particularly limited and are each generally 0.4 to 2.8 cm. When the corners are rounded, the fit and suitability of the adhesive tape 3 to the skin are enhanced, thus making it difficult for the adhesive tape 3 to become detached from the skin. Also with this configuration, the adhesive tape 3 can be applied so as to relieve pressure around the nail 51 as in the first embodiment and the second embodiment.

Figure 5:
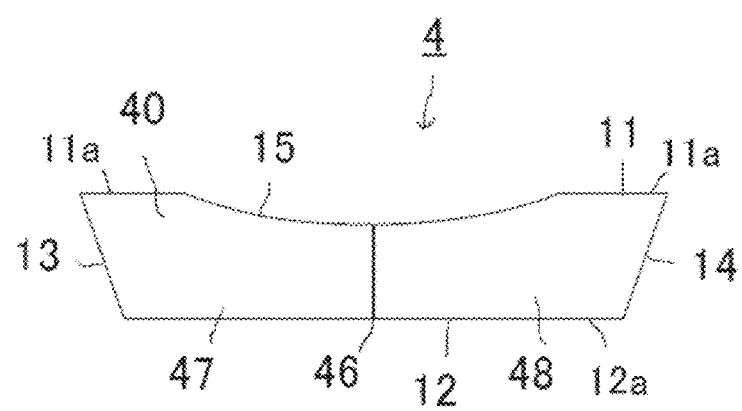
FIG. 5 is a plan view of an adhesive tape according to a fourth embodiment of the present invention.

With reference to FIG. 5, the adhesive tape according to the fourth embodiment of the present invention is described below. Elements that are the same as those of the adhesive tape 1 according to the first embodiment are denoted with the same reference numerals as those shown in FIG. 1, and the descriptions are omitted.

The adhesive tape 4 according to the fourth embodiment is different from the adhesive tape 1 according to the first embodiment in that a release material layer 40 has a slit 46 at the center of a recess 15 of an upper edge 11, i.e., at a location on the central axis Ax perpendicular to the longitudinal direction of the adhesive tape 4, and that the release material layer 40 is composed of two portions 47 and 48 separated by the slit 46. Also with this configuration, the adhesive tape 4 can be used irrespective of whether the affected area 52 is either on the right or left side of the nail 51, because the release material layer 40 can be peeled off not only from the portion 47, but also from the portion 48 at the position of the slit 46. In the fourth embodiment, the recess 15 is shallower than that in the first embodiment, and the overall dimensions are smaller than those in the first embodiment. Such an embodiment is also within the scope of the present invention.

Figure 6:
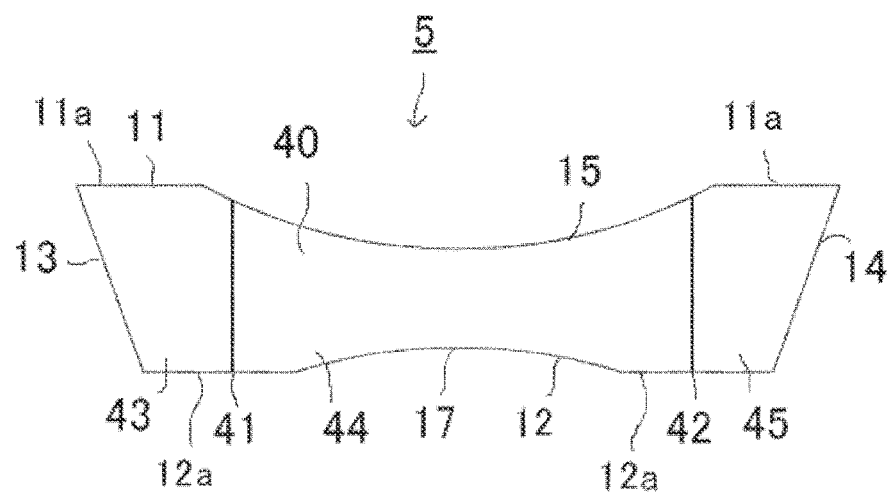
FIG. 6 is a plan view of an adhesive tape according to a fifth embodiment of the present invention.

With reference to FIG. 6, the adhesive tape according to the fifth embodiment of the present invention is described below. Elements that are the same as those of the adhesive tape 1 according to the first embodiment are denoted with the same reference numerals as those shown in FIG. 1, and the descriptions are omitted.

In the adhesive tape 5 according to the fifth embodiment, the longer of two edges 11 and 12 extending in the longitudinal direction of the adhesive tape 5, i.e., the upper edge 11, includes a recess 15, and, not only that, the shorter of the two edges 11 and 12 extending in the longitudinal direction of the adhesive tape 5, i.e., the lower edge 12, also includes a recess 17 curved toward the inside of the adhesive tape 5. Since the adhesive tape 5 has the recess 17 also on the lower edge 12 side, the area of contact between the adhesive tape 5 and the skin of a patient can be reduced. Also with this configuration, the adhesive tape 5 can be applied so as to relieve pressure around the nail 51 as in the first to fourth embodiments.

Figure 7:
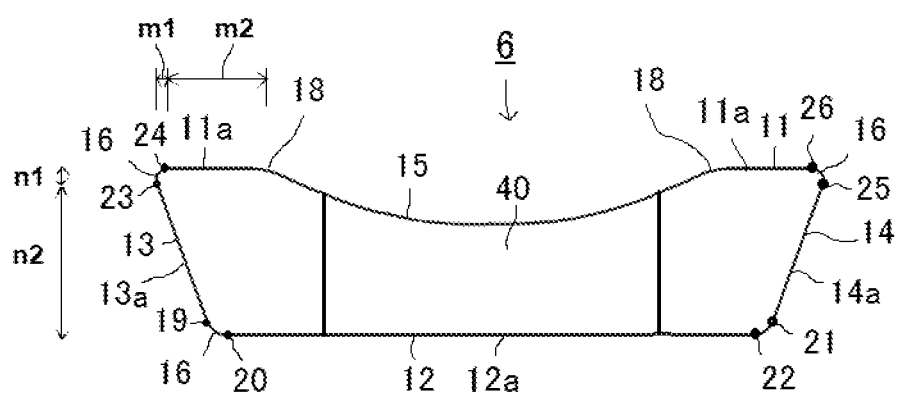
FIG. 7 is a plan view of an adhesive tape according to a sixth embodiment of the present invention.

With reference to FIG. 7, the adhesive tape according to the sixth embodiment of the present invention is described below. The adhesive tape 6 according to the sixth embodiment is a modification of the adhesive tape 3 according to the third embodiment of FIG. 4. Elements that are the same as those of the adhesive tape 3 according to the third embodiment are denoted with the same reference numerals as those shown in FIG. 4, and the descriptions are omitted.

In the adhesive tape 6 according to the sixth embodiment, connection portions 18 between an upper edge 11 and a recess 15 are further rounded so as to form a continuous substantially curved line.

The curve connecting an end point 19 at the lower end of a substantially straight portion 13a of a left edge 13 and an end point 27 of a substantially straight parallel portion 12a of a lower edge 12 can be set as desired. The curve connecting an end point 21 at the lower end of a substantially straight portion 14a of a right edge 14 and an end point 22 of the substantially straight parallel portion 12a of the lower edge 12, the curve connecting an end point 23 at the upper end of the substantially straight portion 13a of the left edge 13 and an end point 24 of a substantially straight parallel portion 11a of the upper edge 11, and the curve connecting an end point 25 at the upper end of the substantially straight portion 14a of the right edge 14 and an end point 26 of a substantially straight parallel portion 11a of the upper edge 11 can also be set as desired. For example, the radius of curvature of each curve may be set to 1 to 10 mm.

The length of two straight edges and the size of rounded corner 16 between them can be changed as desired. For example, the m1:m2 length ratio may be about 1:1 to 1:20, where m1 represents the length in the longitudinal direction of the adhesive tape 6 of a rounded corner 16 between the end point 23 and the end point 24, and m2 represents the length of a parallel portion 11a. The n1:n2 length ratio may be about 1:1 to 1:20, where n1 represents the length of the rounded corner 16 in the width direction of the adhesive tape 6, and n2 represents the length of the substantially straight portion 13a of the left edge 13 (the substantially straight portion 14a of the right edge 14) in the width direction of the adhesive tape 6.

Figure 8:
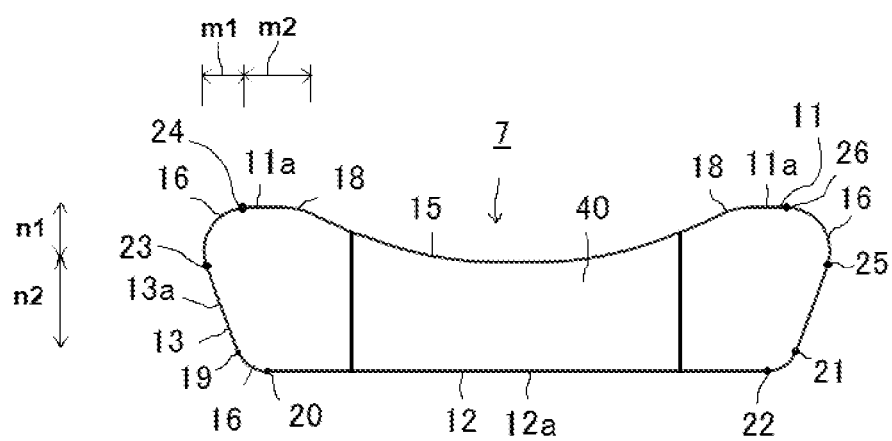
FIG. 8 is a plan view of an adhesive tape according to a seventh embodiment of the present invention.

With reference to FIG. 8, the adhesive tape according to the seventh embodiment of the present invention is described below. The adhesive tape 7 according to the seventh embodiment is also a modification of the adhesive tape 3 according to the third embodiment of FIG. 4. Elements that are the same as those of the adhesive tape 3 according to the third embodiment are denoted with the same reference numerals as those shown in FIG. 4, and the descriptions are omitted.

In the adhesive tape 7 according to the seventh embodiment, connection portions 18 between an upper edge 11 and a recess 15 are rounded so as to form a continuous substantially curved line. The length of the curve between an end point 19 at the lower end of a substantially straight portion 13a of a left edge 13 and an end point 27 of a substantially straight parallel portion 12a of a lower edge 12 is larger than that in the sixth embodiment of FIG. 7. The length of the curve between an end point 23 at the upper end of the substantially straight portion 13a of the left edge 13 and an end point 24 of a substantially straight parallel portion 11a of the upper edge 11 is also larger than that in the sixth embodiment of FIG. 7. The ranges of the m1:m2 length ratio and the n1:n2 length ratio are as described in the explanation of the adhesive tape according to the sixth embodiment of FIG. 7.

The first to seventh embodiments have been described as examples of the present invention; however, the present invention is not limited to these embodiments, and various modifications as described below are possible.

The recess 15 may be formed in another curve shape in plan view, such as a parabola or a hyperbola, instead of a circular arc in plan view.

Although in the first to seventh embodiments, the base material 20, the adhesive layer 30, and the release material layer 40 are shown as being of the same size, the release material layer 40 may be larger than the base material 20 and the adhesive layer 30. In particular, the release material layer 40 being larger on the outer side of the edges 13 and 14, enables the release material layer 40 to be easily peeled off from the adhesive layer 30, does not become obstructive in application, and is thus preferable.

The configuration of the rounded corners 16 in the adhesive tape 3 according to the third embodiment, the adhesive tape 6 according to the sixth embodiment, and the adhesive tape 7 according to the seventh embodiment may be applied to the adhesive tapes 1, 2, 4, and 5 according to the first, second, fourth, and fifth embodiments or may be applied to any adhesive tape included within the scope of the invention. In addition, not all of the four corners 16 need to be rounded; one, two, or three corners 16 may be rounded.

In the adhesive tapes according to the first to fifth embodiments, all connection portions between edges and adjacent edges may be shaped to have a continuous substantially curved surface as in the adhesive tape 6 according to the sixth embodiment and the adhesive tape 7 according to the seventh embodiment. The curvature of the curved surface of the connection portion between an edge and an adjacent edge may be changed as desired.

An additional layer may be provided on the base material 20, between the base material 20 and the adhesive layer 30, and between the adhesive layer 30 and the release material layer 40.

Figure 9:
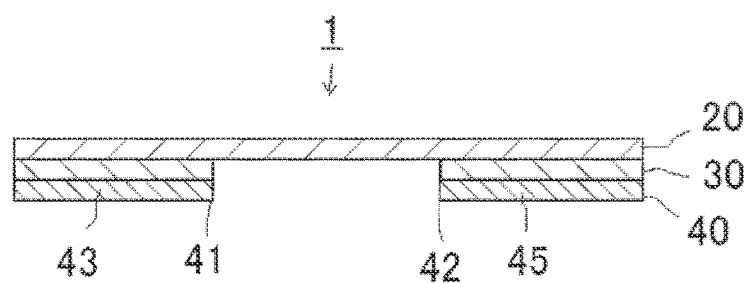
FIG. 9 is a cross-sectional view of an adhesive tape of another example of the present invention.

As shown in FIG. 9, it may also be possible to not provide the adhesive layer 30 in the central portion in the longitudinal direction of the adhesive tape 1. This configuration enables the skin to be more easily pulled by the base material 20 when the adhesive tape 1 is applied to the skin.

One or more slits similar to the slits 41, 42, and 46 may be provided in the release material layer 40, or the slits 41, 42, and 46 may be omitted.

The three portions 43, 44, and 45 of the release material layer or the two portions 47 and 48 of the release material layer may have a configuration in which they are stacked on the adhesive layer 30 such that edge portions overlap with each other.

The slit(s) of the release material layer 40 do not need to be completely cut, and, for example, may be slit(s) in a dotted line or slit(s) in which one or more areas are left uncut.

In the first to seventh embodiments, the adhesive tapes are described for the treatment, i.e., care, of paronychia; however, they can be used for the prevention and/or treatment of inflammation around nails, in particular, for the prevention of increase in severity of inflammation around nails and/or for pain relief. The adhesive tapes may also be used for the prevention and/or treatment of symptoms around the nail 51, such as the treatment of ingrown nails, other than paronychia.

The adhesive tape of the present invention, which includes the adhesive tapes 1 to 7 according to the first to seventh embodiments and adhesive tapes according to modifications of these embodiments, may be used not only for the treatment of inflammation, but also for keeping the skin away from nails. For example, the adhesive tape of the present invention may be used when a drug is applied near nail grooves.

The thumb is shown in FIG. 2(A) and FIG. 2(B); however, the adhesive tape of the present invention may be applied to the index, middle, ring, and/or little finger, or applied to one or more of the five toes.

The present invention includes a kit for treating paronychia, comprising the adhesive tape of the present invention, which includes the adhesive tapes 1 to 7 according to the first to seventh embodiments and adhesive tapes according to modifications of these embodiments, and one of or both of the following: instructions for appropriately performing the prevention and/or treatment of paronychia; a check sheet for checking the state of an affected area. The instructions are the same as those described in the method of use of the adhesive tape 1 according to the first embodiment of FIG. 1. For example, the instructions include directions to peel off the release material layer 40 of the adhesive tape of the present invention, to place the adhesive tape on a site of the skin on the side of an affected area, and to apply the adhesive tape to the finger helically. The check sheet for recording the state of an affected area is a check sheet in which the state of an affected area is recorded daily and with which the patient, family, etc. can easily check the state of the affected area.

In one embodiment, the kit for treating paronychia comprises the adhesive tape of the present invention; either instructions for appropriately performing the prevention and/or treatment of paronychia, or a check sheet for recording the state of an affected area, or both; a container containing a humectant; a cotton swab; and a protective material, such as a bandage for fingers or a fingerstall. The kit may also comprise another adhesive tape of a hydrocolloid or the like or another tape material. The other adhesive tape may be partially applied when there is an injury in an affected area, or applied so as to cover the entire portion after application of the adhesive tape of the present invention.

As the humectant, known humectants can be used. Examples include Hirudoid (registered trademark) lotions, white petrolatum, and the like. The protective material, such as a bandage for fingers or a waterproof fingerstall, is used for protecting the surrounding area of a finger portion, including an affected area, after application of the adhesive tape to the skin. The amounts of adhesive tapes, humectant, cotton swabs, and protective material, such as a bandage or a waterproof fingerstall, in the kit can be set according to a period during which the user will use the kit. For example, if the period is 30 days, the kit may comprise 30 adhesive tapes, a 30-day amount of humectant, 30 cotton swabs, and a 30-day amount of protective material.

FIG. 10 shows an example of the check sheet for recording the state of an affected area. The check sheet 100 includes spaces 101 for the date, items 102 for observation results of an affected area, and items 103 for self-care. Although in this example, a week from Monday to Sunday is shown in a row, the form of the spaces 101 for the date is not particularly limited. For example, the form may be the following: dates on which the state of an affected area is recorded are put in blanks, or dates from the first date to the last date of a month are arranged in a column.

Examples of the items 102 for observation results of an affected area include whether there is pain around the nail, swelling around the nail, cracking of the skin, itching of the skin, and other findings regarding the skin, and the like. In the items for observation results of an affected area, for example, the condition of the affected area may be described, the extent of the condition of the affected area may be described, or numerical values obtained when the condition of the affected area is graded may be entered.

Examples of the items 103 for self-care include whether an affected area is washed or not, whether an affected area is moisturized or not, taping by using the adhesive tape of the present invention, and other self-care. Whether washing is done is determined, for example, based on whether the affected area has been washed with a weakly acidic or low-irritant cleaning agent not less than a predetermined number of times (for example, one or more times) a day. The type of cleaning agent and the number of times washing is done can be changed. Whether moisturizing is done is determined based on whether the affected area has been moisturized with a humectant not less than a predetermined number of times (for example, five or more times) a day. The humectant is preferably the humectant provided in the kit; however, another humectant suitable for the prevention and/or treatment of the affected area may be used. The type of humectant and the number of times moisturizing is done can be changed. Whether taping by using the adhesive tape of the present invention is done is determined based on whether the taping has been replaced not less than a predetermined number of times in a predetermined period of time (for example, once a day).

Inflammation around nails may become severe by the time when an outpatient sees a doctor because the medical practitioner cannot check the state of the affected area every day. The kit of the present invention comprises instructions for a patient, family, or the like to appropriately perform the prevention and/or treatment of paronychia, for example, at home, and/or comprises a check sheet with which the daily state of an affected area can be easily checked by a patient, family, or the like. Thus, this enables the prevention of increase in severity of the affected area and enables the state of the affected area to be reported to a medical practitioner early and smoothly when the affected area becomes severe.

The invention claimed is:

1. An adhesive tape comprising a base material layer, an adhesive layer, and a release material layer,
   wherein the adhesive tape has a longitudinal direction and two edges extending in the longitudinal direction of the adhesive tape include parallel portions, each edge extending between two ends,
   the length of one of the two edges is greater than the length of the other,
   the ends of the two edges are connected to the ends of two other edges,
   two angles formed between the longer edge of the two edges extending in the longitudinal direction and the two other edges are acute angles,
   the longer edge of the two edges extending in the longitudinal direction includes a recess toward the shorter edge, and
   the shorter edge of the two edges extending in the longitudinal direction includes a substantially straight parallel portion except for both its ends.

2. The adhesive tape according to claim 1, which has a shape that is symmetrical about a central axis perpendicular to the longitudinal direction of the adhesive tape.

3. The adhesive tape according to claim 2, wherein the release material layer is composed of three portions separated by two slits that are parallel to and equidistant from the central axis, or is composed of two portions separated by one slit on the central axis.

4. The adhesive tape according to claim 1, which is an adhesive tape for the prevention and/or treatment of inflammation around a nail.

5. A kit for treating paronychia, comprising the adhesive tape according to claim 1 and a check sheet for recording a state of an affected area.

6. The kit according to claim 5, which further comprises a humectant, a cotton swab, and a protective material.

7. The adhesive tape according to claim 1, wherein each of the two other edges is substantially straight over its entire length or substantially straight except for both its ends.

8. The adhesive tape according to claim 1, wherein the two other edges each have a length of 0.8 to 3 cm.

9. The adhesive tape according to claim 1, wherein all of the ends are rounded in a substantially curved shape, and connection portions between the longer edge and the recess are rounded to form a continuous substantially curved line.

10. The adhesive tape according to claim 9, wherein a radius of curvature of each curve of the ends is set to 1 to 10 mm.

11. The adhesive tape according to claim 9, wherein an m1:m2 length ratio is 1:1 to 1:20, where m1 represents the length of the rounded corner in the longitudinal direction of the adhesive tape, and m2 represents the length of a parallel portion in the longer edge.

12. The adhesive tape according to claim 9, wherein an n1:n2 length ratio is 1:1 to 1:20, where n1 represents the length of the rounded corner in the width direction of the adhesive tape, and n2 represents the length of the substantially straight portion of each of the two other edges in the width direction of the adhesive tape.

* * * * *